US010285642B2

(12) United States Patent
Ahmad et al.

(10) Patent No.: US 10,285,642 B2
(45) Date of Patent: May 14, 2019

(54) BREATH ANALYSIS DEVICE WITH WATCH BAND THAT HOLDS BREATH ANALYSIS CARTRIDGES

(71) Applicant: Invoy Holdings, LLC, Aliso Viejo, CA (US)

(72) Inventors: Lubna Ahmad, Chandler, AZ (US); Salman Ahmad, Chandler, AZ (US); Zachary Smith, Phoenix, AZ (US)

(73) Assignee: Invoy Holdings, LLC, Aliso Viejo, CA (US)

( * ) Notice: Subject to any disclaimer, the term of this patent is extended or adjusted under 35 U.S.C. 154(b) by 133 days.

(21) Appl. No.: 15/423,382

(22) Filed: Feb. 2, 2017

(65) Prior Publication Data
US 2017/0215795 A1    Aug. 3, 2017

Related U.S. Application Data

(60) Provisional application No. 62/290,689, filed on Feb. 3, 2016.

(51) Int. Cl.
*A61B 5/08* (2006.01)
*A61B 5/00* (2006.01)
*A61B 5/097* (2006.01)

(52) U.S. Cl.
CPC .............. *A61B 5/681* (2013.01); *A61B 5/082* (2013.01); *A61B 5/097* (2013.01); *A61B 5/6822* (2013.01);
(Continued)

(58) Field of Classification Search
CPC ......... A61B 5/082; A61B 5/097; A61B 5/681; A61B 5/6822; A61B 5/6824
See application file for complete search history.

(56) References Cited

U.S. PATENT DOCUMENTS

| 4,147,514 A | 4/1979 | Magers et al. |
|---|---|---|
| 4,844,867 A | 7/1989 | Bather |

(Continued)

FOREIGN PATENT DOCUMENTS

| EP | 1 524 522 | 4/2005 |
|---|---|---|
| WO | WO 03/039367 | 5/2003 |

(Continued)

OTHER PUBLICATIONS

U.S. Appl. No. 13/052,963, filed Mar. 21, 2011, Ahmad et al.
(Continued)

*Primary Examiner* — Puya Agahi
(74) *Attorney, Agent, or Firm* — Knobbe, Martens, Olson & Bear, LLP

(57) ABSTRACT

A wearable breath analysis device is disclosed that may be worn, for example, around the neck or wrist of a user. The wearable device may be a stand-along device (in which case it may include a display that provides a user interface), or may operate in conjunction with a smartphone or other command device. The wearable device may include auditory and/or vibratory notice and communications features or capabilities, for example, such as a reminder or notice to conduct a breath analyte measurement, instructions to the user in the course of conducting the measurement, and notice of the breath analyte measurement results. The auditory or vibratory notice may be provided at the wearable, and/or at the command device where a command device is used. Related methods also are provided.

11 Claims, 9 Drawing Sheets

(52) U.S. Cl.
CPC .......... *A61B 5/7405* (2013.01); *A61B 5/7455* (2013.01); *A61B 5/002* (2013.01)

(56) References Cited

U.S. PATENT DOCUMENTS

| | | | |
|---|---|---|---|
| 4,931,404 A | 6/1990 | Kundu | |
| 4,970,172 A | 11/1990 | Kundu | |
| 5,071,769 A | 12/1991 | Kundu et al. | |
| 5,174,959 A | 12/1992 | Kundu et al. | |
| 5,465,728 A | 11/1995 | Phillips | |
| 5,834,626 A | 11/1998 | De Castro et al. | |
| 6,010,459 A | 1/2000 | Silkoff et al. | |
| 6,067,989 A | 5/2000 | Katzman | |
| 6,190,858 B1 | 2/2001 | Persaud | |
| 6,206,837 B1 | 3/2001 | Brugnoli | |
| 6,221,026 B1 | 4/2001 | Phillips | |
| 6,234,006 B1 | 5/2001 | Sunshine et al. | |
| 6,254,547 B1 | 7/2001 | Phillips | |
| 6,454,723 B1 | 9/2002 | Montagnino | |
| 6,540,691 B1 | 4/2003 | Phillips | |
| 6,582,376 B2 | 6/2003 | Baghdassarian | |
| 6,599,253 B1 | 7/2003 | Baum et al. | |
| 6,607,387 B2 | 8/2003 | Mault | |
| 6,609,068 B2 | 8/2003 | Cranley et al. | |
| 6,629,934 B2 | 10/2003 | Mault et al. | |
| 6,658,915 B2 | 12/2003 | Sunshine et al. | |
| 6,726,637 B2 | 4/2004 | Phillips | |
| 6,841,391 B2 | 1/2005 | Lewis et al. | |
| 6,981,947 B2 | 1/2006 | Melker | |
| 7,052,854 B2 | 5/2006 | Melker et al. | |
| 7,104,963 B2 | 9/2006 | Melker et al. | |
| 7,220,387 B2 | 5/2007 | Flaherty et al. | |
| 7,300,408 B2 | 11/2007 | Hancock et al. | |
| 7,364,551 B2 | 4/2008 | Allen et al. | |
| 7,533,558 B2 | 5/2009 | Flaherty et al. | |
| 7,794,994 B2 | 9/2010 | Cranley et al. | |
| 7,837,936 B1 | 11/2010 | Martin | |
| 7,920,998 B2 | 4/2011 | Brown | |
| 7,976,467 B2 | 7/2011 | Young et al. | |
| 8,021,308 B2 | 9/2011 | Carlson et al. | |
| 8,036,708 B2 | 10/2011 | Oozeki | |
| 8,286,088 B2 | 10/2012 | Shaffer et al. | |
| 8,287,454 B2 | 10/2012 | Wolpert et al. | |
| 8,342,178 B2 | 1/2013 | Hengstenberg et al. | |
| 8,399,837 B2 | 3/2013 | Robbins et al. | |
| 8,514,086 B2 | 8/2013 | Harper et al. | |
| 8,680,974 B2 | 3/2014 | Meiertoberens et al. | |
| 8,722,417 B2 | 5/2014 | Ahmad | |
| 8,816,862 B2 | 8/2014 | Harper et al. | |
| 8,848,189 B2 | 9/2014 | Atkin et al. | |
| 8,871,521 B2 | 10/2014 | Akers | |
| 8,917,184 B2 | 12/2014 | Smith et al. | |
| 9,170,225 B2 | 10/2015 | Dutta et al. | |
| 9,173,595 B2 | 11/2015 | Böhm et al. | |
| 9,299,238 B1 | 3/2016 | Ahmad et al. | |
| 9,341,632 B1 | 5/2016 | Ahmad et al. | |
| 9,351,684 B1 | 5/2016 | Ahmad et al. | |
| 9,486,169 B1 | 11/2016 | Ahmad | |
| 2003/0208133 A1 | 11/2003 | Mault | |
| 2004/0018114 A1 | 1/2004 | Wang et al. | |
| 2007/0245810 A1 | 10/2007 | Carter et al. | |
| 2007/0258894 A1 | 11/2007 | Melker et al. | |
| 2008/0008666 A1 | 1/2008 | Phillips | |
| 2008/0053194 A1 | 3/2008 | Ahmad | |
| 2008/0234553 A1 | 9/2008 | Urman et al. | |
| 2009/0054799 A1 | 2/2009 | Vrtis et al. | |
| 2010/0121210 A1* | 5/2010 | Lindner | G01N 33/497 600/532 |
| 2010/0152545 A1* | 6/2010 | Ramsay | A61B 5/0002 600/301 |
| 2010/0301197 A1 | 12/2010 | Boyle | |
| 2011/0028091 A1 | 2/2011 | Higgins et al. | |
| 2011/0098590 A1 | 4/2011 | Garbutt et al. | |
| 2012/0071737 A1 | 3/2012 | Landini et al. | |
| 2012/0295595 A1 | 11/2012 | Gibori et al. | |
| 2013/0231711 A1 | 9/2013 | Kaib | |
| 2013/0253358 A1 | 9/2013 | Phillips | |
| 2014/0276100 A1* | 9/2014 | Satterfield | A61B 5/082 600/476 |
| 2014/0366610 A1 | 12/2014 | Rodriguez | |
| 2015/0073233 A1 | 3/2015 | Rich et al. | |
| 2015/0168307 A1 | 6/2015 | Kück et al. | |
| 2015/0186092 A1* | 7/2015 | Francis | G06F 3/1423 345/520 |
| 2015/0289782 A1 | 10/2015 | Peverall et al. | |
| 2016/0146779 A1 | 5/2016 | Gallagher et al. | |
| 2016/0150995 A1 | 6/2016 | Ratto et al. | |
| 2016/0157779 A1* | 6/2016 | Baxi | A61B 5/6831 600/301 |
| 2017/0014048 A1* | 1/2017 | Wilke | A61B 5/082 |
| 2017/0020443 A1* | 1/2017 | Fein | A61B 5/486 |

FOREIGN PATENT DOCUMENTS

| | | |
|---|---|---|
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2015/134390 | 9/2015 |

OTHER PUBLICATIONS

U.S. Appl. No. 15/340,811, filed Nov. 1, 2016, Ahmad et al.

Ahmad, L. et al., "Design of a Breath Ketone Sensor for Obesity Management", Poster Presentation, Fall Meeting of the Biomedical Engineering Society, 2004, in 3 pages.

Barnett, D. et al., "Breath acetone and blood sugar measurements in diabetes", Clinical Science, vol. 37 (1969), in 1 page.

"CMS Operator Guide", CMS Operator Training 0108, dated Apr. 19, 2002, in 10 pages. URL: http://www.buydraegertubes.com/ds/cms-ops-guide.pdf.

Crofford, O. et al., "Acetone in Breath and Blood", Transactions of the American Clinical and Climatological Association, vol. 88 (1977), in 12 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Drager CMS Production Information (document properties of document indicate that the document was created on Dec. 1, 2008), in 4 pages. URL: http://www.draeger.com/sites/assets/PublishingImages/Products/cin_chip_measurement_system/US/cms-ds-pi-9044337-en-us.pdf.

DragerTubes & Accuro Pump Production Information (document properties of document indicate that the document was created on Nov. 11, 2008), in 4 pages. URL: http://www.draeger.com/sites/assets/PublishingImages/Products/cin_accuro/US/081209-pi-DetectorTubes-22-10-2008-en.pdf.

Dubowski, K. et al., "Response of Breath-Alcohol Analyzers to Acetone: Further Studies", Journal of Analytical Toxicology, vol. 8, Sep./Oct. 1984, in 4 pages.

Gervais, T. et al., "Mass transport and surface reactions in microfluidic systems", Chemical Engineering Science, vol. 61 (2006), in 20 pages.

Ketonix US, "Ketonix 2015 Blue Specifications", 2015, in 2 pages. URL:https://www.ketonix.com/index.php/product-2/ketonix-2015-blue.

Ketonix, "Ketonix data for Michel Lundell", 2015, in 1 page. URL: https://www.ketonix.com.

Khan, A. et al. "Evaluation of a bedside blood ketone sensor: the effects of acidosis, hyperglycaemia and acetoacetate on sensor performance", Diabetic Medicine, vol. 21 (2004), in 5 pages.

Kundu, S. et al., "Breath Acetone Analyzer: Diagnostic Tool to Monitor Dietary Fat Loss", Clinical Chemisty, vol. 39 (1993), in 6 pages.

Kundu, S. K. et al., "Novel Solid-Phase Assay of Ketone Bodies in Urine", Clinical Chemistry, vol. 37 (1991), in 5 pages.

Kupari, M. et al., "Breath Acetone in Congestive Heart Failure", The American Journal of Cardiology, vol. 76, Nov. 15, 1995, in 3 pages.

(56) References Cited

OTHER PUBLICATIONS

Landini, B. et al., "Breath Acetone Concentration Measured Using a Palm-Size Enzymatic Sensor System", IEEE Sensors Journal, vol. 9, Dec. 2009, in 6 pages.
Landini, B. et al., "Effect of Exhalation Variables on the Current Response of an Enzymatic Breath Acetone Sensing Device", IEEE Sensors Journal, vol. 10, Jan. 2010, in 6 pages.
Likhodii, S., et al., "Breath Acetone as a Measure of Systemic Ketosis Assessed in a Rat Model of the Ketogenic Diet", Clinical Chemistry, vol. 48 (2002), in 6 pages.
Loken, S. C., "Breath Acetone and Ketone Metabolism in Obese and Diabetic Mice", Diabetes, vol. 25 (1976), in 1 page.
"Figaro Gas Sensor TGS 822", Figaro Engineering Inc., Mar. 1987, in 10 pages.
"MiniMed 530G System User Guide", Medtronic MiniMed, Inc., 2012, in 312 pages.
Musa-Veloso, K. et al., "Breath acetone is a reliable indicator of ketosis in adults consuming ketogenic meals", The American Journal of Clinical Nutrition, vol. 76 (2002), in 6 pages.
Schwarz, K., et al., "Breath acetone—aspects of normal physiology related to age and gender as determined in a PTR-MS study", Journal of Breath Research, vol. 3 (2009), in 9 pages.
Wang, L. et al., "Nanosensor Device for Breath Acetone Detection", Sensor Letters, vol. 8 (2010), in 4 pages.
Wang, L., "Tailored synthesis and characterization of selective metabolite-detecting nanoprobes for handheld breath analysis", Dissertation Ph. D. Thesis, Stony Brook University, Dec. 2008, in 127 pages.
Yoon, S. et al., "Active control of the depletion boundary layers in microfluidic electrochemical reactors", Lab on a Chip, vol. 6 (2006), in 9 pages.

\* cited by examiner

US 10,285,642 B2

BREATH ANALYSIS DEVICE WITH WATCH BAND THAT HOLDS BREATH ANALYSIS CARTRIDGES

INCORPORATION BY REFERENCE TO ANY PRIORITY APPLICATIONS

This application claims the benefit of priority of U.S. Provisional Pat. Appl. No. 62/290,689, filed on Feb. 3, 2016. All of the above applications are incorporated by reference herein and are to be considered a part of this specification. Any and all applications for which a foreign or domestic priority claim is identified in the Application Data Sheet as filed with the present application are hereby incorporated by reference under 37 CFR 1.57.

BACKGROUND

Field of the Invention

The present invention relates to apparatus, systems and methods for sensing or measuring chemical components or constituents (analytes) in the breath of a patient or "user," and more specifically to breath analysis devices that comprise or are incorporated into a wearable device.

Description of the Related Art

The importance or benefits of measuring the presence or concentration of chemical constituents in the body (analytes) to aid in assessing a person's physiological or pathophysiological state is well known. Conventional approaches to chemically-based diagnostic screening and analysis for blood gases involve blood tests and urine tests. Blood tests generally require that blood be drawn and chemically tested, typically in a lab. Urine tests involve similar drawbacks. A urine sample must be collected and tested, again, typically in a lab.

The use of breath as a source of chemical analysis can overcome many of these drawbacks. The breath sample can be quickly and easily collected, and modern breath analysis devices commonly are small portable devices that can analyze the sample for the target analyte in only minutes.

Many of the currently available breath analysis devices require some level of manual operation. They typically require test set up steps, such as powering up the device, installing a mouthpiece, etc. Most if not all require manual selection (with hand or finger) of Start command to initiate the analyte measurement test. After the test is completed, the results typically are displayed on a display window.

SUMMARY

To address these limitations and advance the art, breath analysis devices, systems and methods are provided that embody a breath analysis device in a "wearable" item. The device, system or method may comprise a wearable that incorporates a breath analysis device together with support features, e.g., data processing features, output displays and so on, so that the device or system is essentially self-contained or stand-alone. Alternatively, the wearable may comprise the breath analysis device, but it is used in a system that includes a physically separate command device, e.g., such as a smart phone.

The wearable preferably comprises auditory and/or haptic (which could include vibratory) notice and communications features or capabilities, for example, such as a reminder or notice to conduct a breath analyte measurement, instructions to the user in the course of conducting the measurement, and notice of the breath analyte measurement results. The auditory or vibratory notice may be provided at the wearable, and/or at the command device where a command device is used.

The invention according to one aspect comprises a wearable that includes a breath analysis device and an auditory and/or vibratory notification device. In a presently preferred embodiment, the wearable comprises a breath analysis device, a breath sample collection conduit, a mouthpiece, an analyte sensor, a processing device, and the auditory and/or vibratory notification device. The wearable also may comprise a transmitter or transceiver device for communicating externally, e.g., to receive data or instructions and to transmit measurement results and related data. The wearable according to this embodiment preferably operates independently as a standalone device, and optionally may operate in conjunction with a command device such as a smart phone, tablet device, laptop or the like. A software or app may be incorporated into wearable, the software or app may be incorporated into the command device where one is employed, or the software or app may be split between the two.

In accordance with another aspect of the invention, a system is provided that comprises a wearable and a command device. The wearable comprises a breath analysis device; it may further comprise other more "traditional" systems, such as earbuds to listen to music, a phone or a Bluetooth headset. The command device, however, which may comprise a smart phone, etc. as described herein above, functions as a controller for the breath analysis device and as a reporting device to the user. The system further comprises an auditory or vibratory notice device at the wearable and/or at the command device.

Related methods also are provided.

BRIEF DESCRIPTION OF THE DRAWINGS

The accompanying drawings, which are incorporated in and constitute a part of the specification, illustrate a presently preferred embodiments and methods of the invention and, together with the general description given above and the detailed description of the preferred embodiments and methods given below, serve to explain the principles of the invention. Of the drawings.

DETAILED DESCRIPTION

Figure 1:
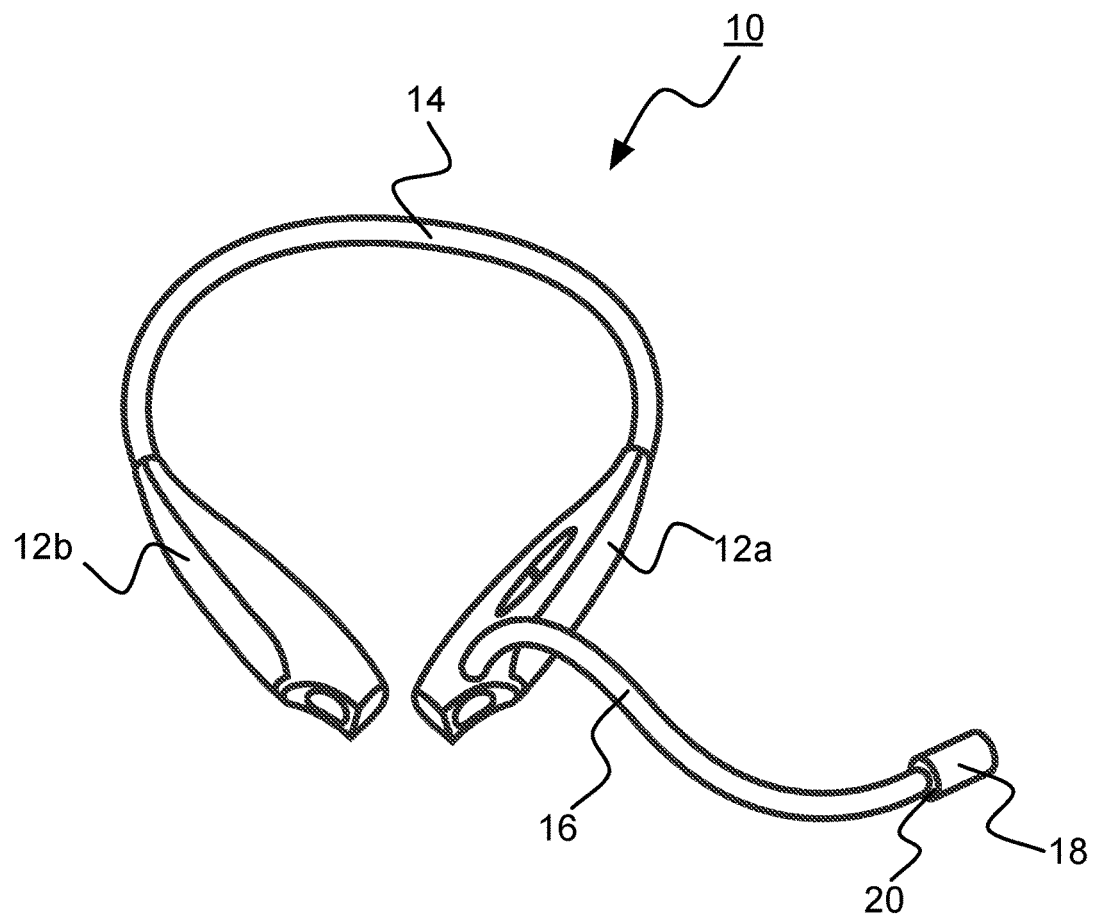
FIG. 1 shows a presently preferred embodiment of a wearable device according to an aspect of the invention.

Reference will now be made in detail to the presently preferred embodiments and methods of the invention as described herein below and as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and will be understood in view of this specification, and appropriate equivalents.

Recently there has been a general trend toward the use of "wearables" with respect to consumer electronics and certain types of health-related devices. Examples include wrist watch devices that include such things as heart rate monitors, blood pressure monitors and the like. A "wearable" as the term is used here is used according to its commonly understood meaning, and includes devices that the user wears on some part of his or her body for relatively extended durations, for example, such as for hours or days, as one might wear a wrist watch. With respect to health-related devices that perform periodic tests, the wearable normally would be worn for periods that extend beyond the specific time actually required to perform the test, although this is not necessarily the case.

Wearables are particularly useful or beneficial for applications in which the wearable is used for a health-related test that is performed multiple times in a relatively short period of time. One example of this type of circumstance involves a diet program. Acetone as a breath analyte has been correlated with fat metabolism. Because a primary goal of many dieters involves burning fat to lose weight, such dieters not infrequently use acetone breath analysis devices to measure their fat burn rate, e.g., as a measure of the effectiveness of their weight loss program. Another class of applications in which regular health-related measurements would be taken involves exercise programs or heavy physical activity.

Currently there are few if any commercially-available or known breath analysis devices that are wearable. Many such devices are laboratory or table top devices. Those that are portable generally are neither wearable nor readily adaptable for wearability.

Moreover, in many of these types of applications, the user is engaged in another activity besides the health-related test, e.g., such as the exercises or physical activities. The user's hands thus may be occupied with the tasks at hand and are unavailable to operate the breath analysis device or it may be very inconvenient to do so. Further, in some breath analysis applications, such as where the user is prostrate and a nasal cannulas has been installed, the user may be physically unable to operate the breath analysis device. Such users often have limited gas or breath flow and no possibility of forced expiration.

Figure 2:
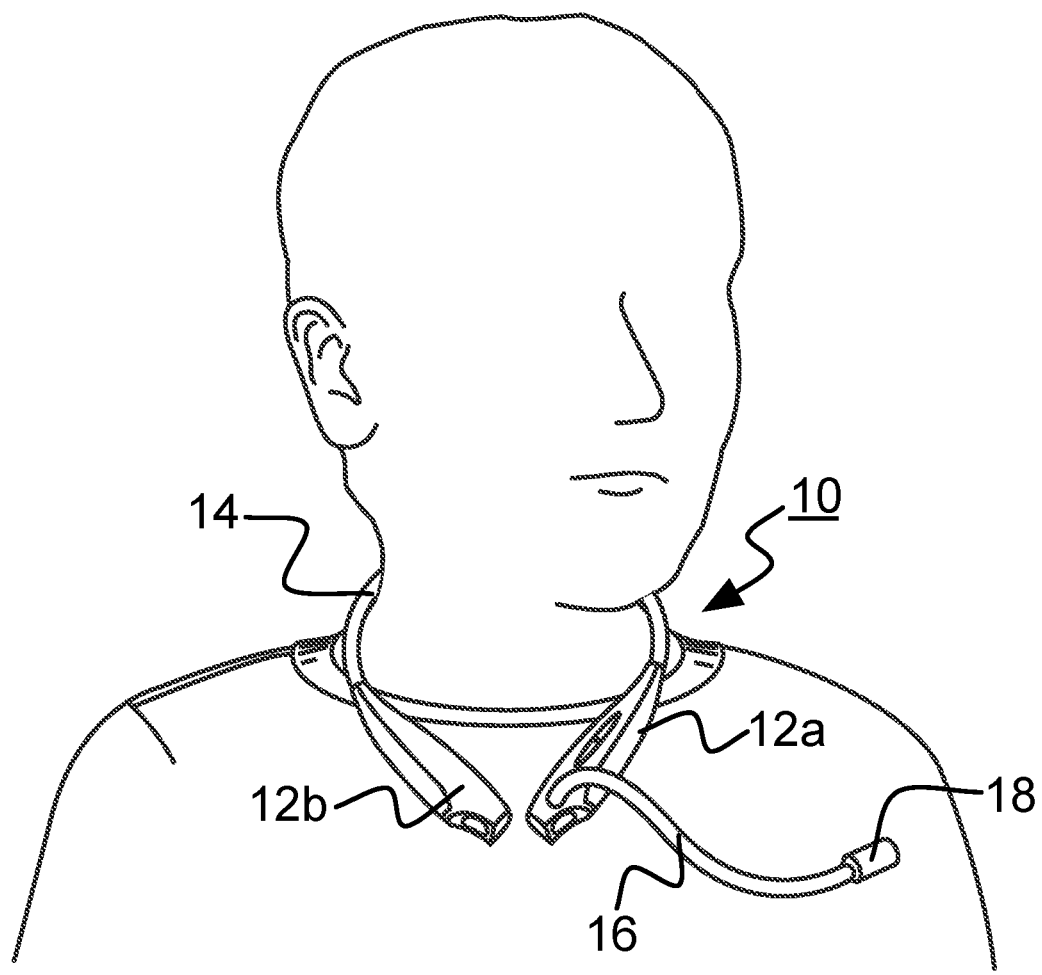
FIG. 2 shows a user wearing the wearable of FIG. 1 prior to conducting a target breath analyte measurement test.
Figure 3:
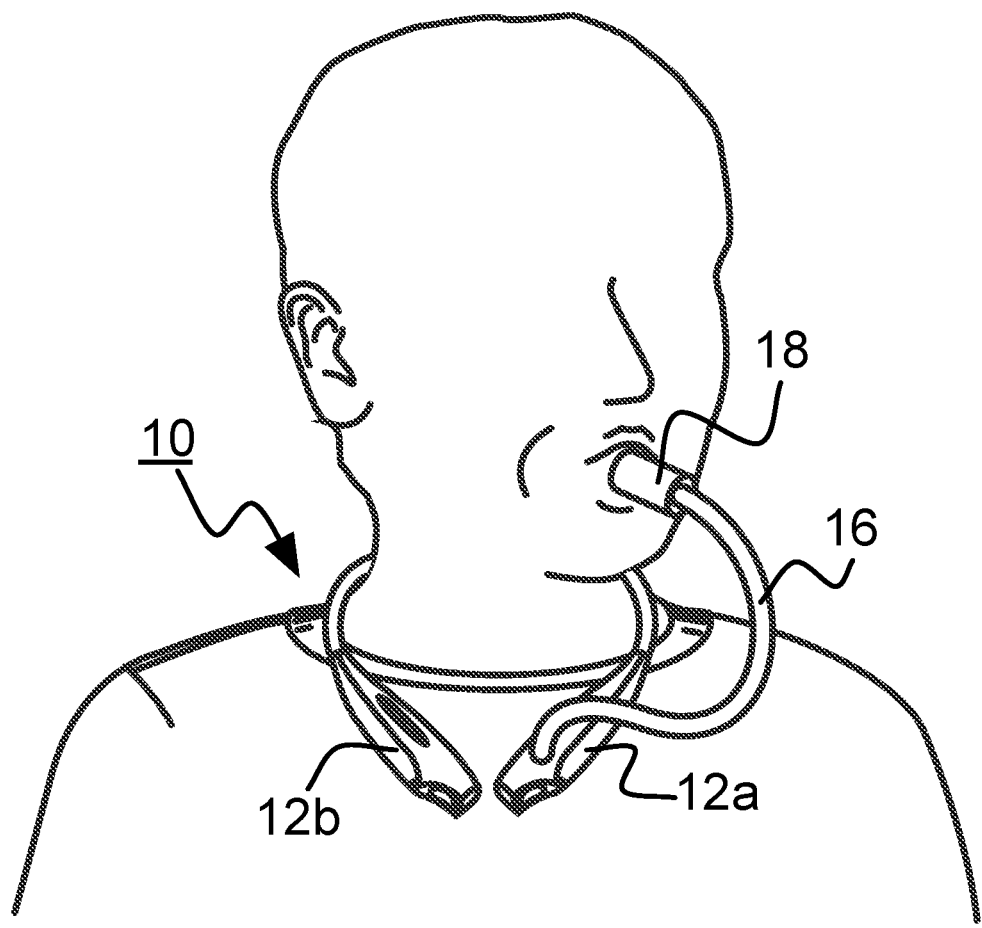
FIG. 3 shows a user wearing the wearable of FIG. 1 while conducting a target breath analyte measurement test.

A wearable device or wearable 10 according to a presently preferred embodiment will now be described with reference to FIGS. 1-6. In this presently preferred but merely illustrative example, wearable device 10 is configured to measure the analyte acetone in the user's or wearer's breath. Wearables according to this aspect of the invention may take any of a number of forms. Examples include headsets, headset-style devices worn around the neck, devices that may be retained in an arm-mounted, neck-mounted or wrist-mounted holster, devices that may be retained in a hip- or waist-mounted holster, and the like. In this embodiment, wearable 10 comprises a headset-style device as shown in FIG. 1 that may be worn around the head or on the neck of a user, e.g., as shown in FIG. 2 (during normal wear but prior to conducting an analyte measurement test) and FIG. 3 (during an analyte measurement test). The headset-style device comprises a body 12 that in turn includes a primary body half 12a and a secondary body half 12b. Body halves 12a and 12b are physically connected by a connecting band 14 such as might be found on a commercially-available headset.

A breath collection tube 16 extends from primary body half 12a. A mouthpiece 18 is detachably disposed at the end of the breath tube that is distal with respect to the body half 12a. Breath collection tube 16 in this embodiment comprises a flexible tubing that is substantially impermeable to air or gases, and particularly to the target analyte. The tubing also preferably is relatively inert to breath and components typically found in breath, including the target analyte.

Figure 4:
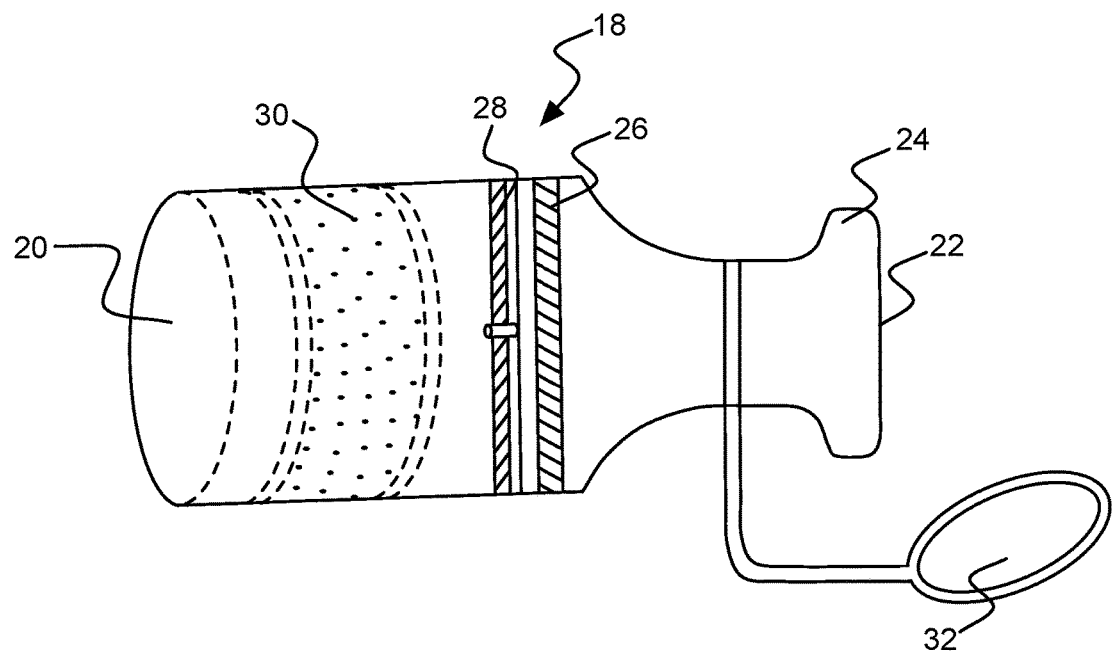
FIG. 4 shows a partial cutaway side view of a mouthpiece for the wearable device of FIG. 1.

Mouthpiece 18 comprises a skirt 20 at its proximal end with respect to body half 12a for detachably coupling to the distal end of tube 16, as shown in FIG. 4. An input opening 22 is located in mouthpiece 18 at its distal end for receiving a breath sample from the user. A bite collar 24 is optionally disposed on the exterior edge of the mouthpiece 18 at its distal end to aid the user in securing the mouthpiece in his or her mouth. Just inside input opening 22 proximally is an optional particle filter 26. Moving proximally toward skirt 20, a one-way valve 28 is disposed to allow the breath sample to pass through proximally (toward tube 16 and body half 12a), but to block flow in the reverse direction. Valve 28 may assume a variety of forms, but in this illustrative embodiment it comprises a flapper or butterfly valve. Immediately proximal to valve 28 is a fluid conditioner, which in this embodiment comprises a desiccant filter 30 for removing moisture from the breath sample as it is inputted. It should be noted that other forms of fluid or flow conditioner may be included in mouthpiece 18, examples of which could include without limitation such things as a flow restrictor, a pressure regulator, a flow truncator (e.g., such as those disclosed in commonly-assigned U.S. Provisional Pat. Appl. No. 62/247,778, entitled "Flow Regulation Device For Breath Analysis And Related Method"), or a device that also captures a deep lung sample (e.g., such as those disclosed in commonly-assigned U.S. patent application Ser. No. 15/340,811 entitled "Flow Regulation Device For Breath Analysis And Related Method") and others. In other embodiments, this may be accomplished through other techniques, such as a flow path with flow resistance sufficient to minimize gas flow into the mouthpiece during the course of the day.

Figure 5:
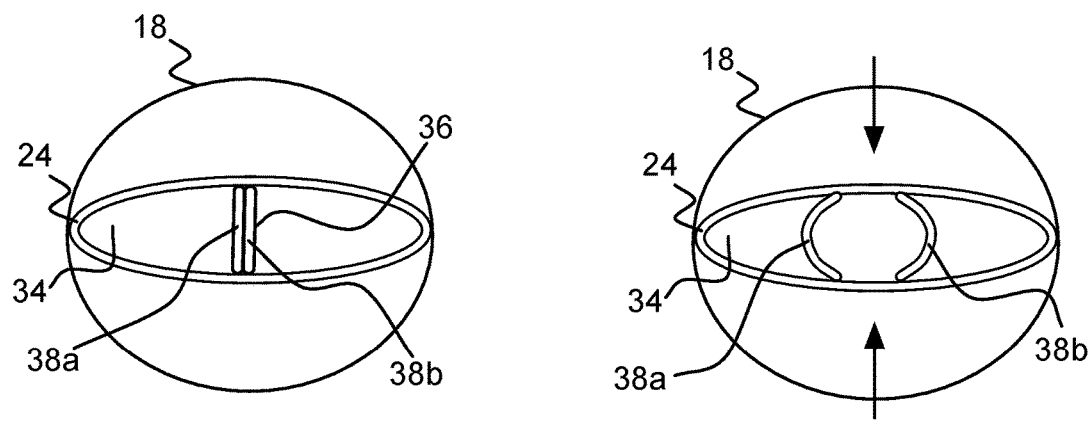
FIG. 5 shows a modification of the mouthpiece of FIG. 4, which modification includes a bite valve.

The input opening 22 of mouthpiece 18 preferably has a cap 32 to facilitate the sanitation of the mouthpiece and to prevent unwanted air, particles, objects, interferents, etc. from entering the interior portions of the mouthpiece. Alternatively or in addition, for example, as shown in FIG. 4, a bite valve 34 may be provided within input opening 22. Bite valve 34 includes a resilient or elastomeric membrane 36, e.g., made of rubber, silicone or the like, with a slit valve 36 incorporated in its center. The slit valve comprises two adjacent and mating resilient flanges 38a and b that are moveable but normally biased closed. In this alternative embodiment, bite collar 24 also is resilient and it is operatively coupled at top and bottom to flanges 38a and b. During normal conditions of non-use, slit valve 36 is biased in its closed position, as shown in FIG. 5, view A. In use, when the user bites the bite collar 24 in the directions shown by the arrows in FIG. 5, view B, vertical or compressive force is applied to flanges 38a and b, which forces them to bend outwardly, thereby creating an opening through which a breath sample may pass.

Figure 6:
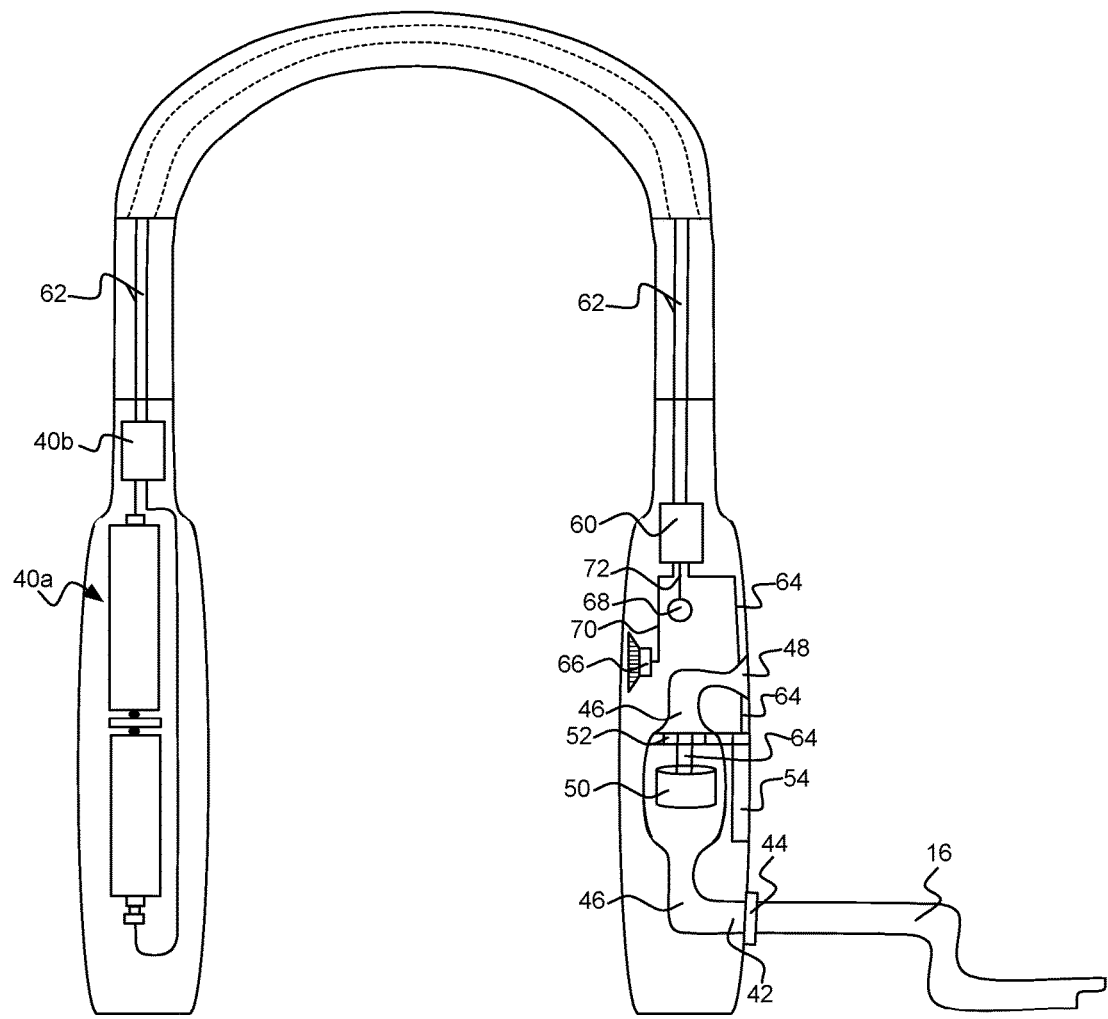
FIG. 6 shows a partial cutaway side view of the wearable of FIG. 1.

A partial cutaway side view of wearable 10 and, more specifically, body 12, is shown in FIG. 6. Primary body half 12a comprises components associated with the breath analysis. Secondary body half 12b in this embodiment comprises a power supply 40, here in the form of a battery pack 40a and optionally a power conditioner 40b for providing voltages as required by the device 10.

Turning to primary body half 12a, breath collection tube 16 enters body half 12a at an input conduit 42 via a coupler 44. Input conduit 42 extends into a main flow channel 46, which in turn extends into an exhaust port 48. An analyte sensor 50 is mounted to a support bracket 52 so that analyte sensor 50 is disposed in main flow channel 46 as air flows through the flow channel comprised of input conduit 42, main flow channel 46 and exhaust port 48. The analyte sensor according to this aspect of the invention may comprise any of a range of suitable sensors for this type of application. Examples include nanoparticle, enzyme-based, thermoelectric, quartz crystal microbalance, optical, colorimetric, metal oxide, semiconductor, magnetoelastic, and gravimetric sensors. Specific yet merely illustrative examples of such sensors include those disclosed in U.S. Pat. No. 6,609,068, entitled "Personal Computer Breath Analyzer For Health-Related Behavior Modification And Method", and U.S. patent application Ser. No. 11/656,338, entitled "Thermoelectric Sensor For Analytes In A Fluid And Related Method" and Ser. No. 13/052,963, entitled "Breath Analysis System, Device And Method Employing Nanoparticle-Based Sensor", and U.S. Provisional Pat. Appl. No. 61/593,862, each of which is hereby incorporated herein by express reference as if fully set forth herein.

In this presently preferred embodiment, analyte sensor 50 comprises a nanoparticle-based sensor, e.g., such as those described in commonly-assigned U.S. Provisional Pat. Appl. No. 62/161,872, entitled "Breath Analysis System, Device And Method Employing Nanoparticle-Based Sensor". In view of the application for which this device 10 is preferably configured, i.e., sensing breath acetone, the preferred analyte sensor in this embodiment is a TGS 822 sensor, commercially available from Figaro USA, Inc. of Arlington Heights, Ill. But, of course, other semiconductor or nanoparticle sensors may be used. An access door 54 is provided in the exterior housing of body half 12a to provide access to sensor 50, e.g., for testing, servicing, replacement, etc.

Primary body half 12a further houses a processor 60 which, for example, may comprise a commercially-available microprocessor or microcontroller capable of the configuration described herein and capable of performing the functions as described herein. Processor 60 is operatively coupled to power supply 40 to receive electrical power from it via a pair of leads 62. Processor 60 also is operatively coupled to analyte sensor 50 to receive the output of the sensor via leads 64. The wearable may also include a non-volatile memory (not shown) which stores program code executed by the processor 60.

Various breath input devices can be used in conjunction with the wearable. Initiation of the test may begin by a mechanical input (e.g., pushing a button), an auditory input (e.g., speaking to initiate the test), activation of a presence sensor (see, e.g., U.S. Pat. application Ser. No. 14/807,828, entitled "Ketone Measurement System Capable Of Detecting And Notifying A User Of Proper Insertion Of Detachable Components", commonly owned by Applicant), or other approaches. A bite valve may be utilized where the user bites a resilient mouthpiece to open a valve in the mouthpiece and then exhales into the tube to initiate the test. A breath input pressure valve may be used. Here, the test is initiated by the user exhaling into a tube. The valve is biased closed, but automatically opens when a threshold pressure is reached in the tube. In another embodiment, a breath input pressure sensor is used. The pressure sensor is disposed in the mouthpiece of in the body of wearable and senses pressure. The test is initiated when a threshold pressure is reached or exceeded.

The breath input devices may be passive or active. In an active input device, a pump may be used to extinguish the contents of a breath bag or breath container.

Wearable device 10 also comprises at least one output device that outputs notifications or information to the user. For example, the wearable may include a haptic signal generator 68 that generates haptic pulses or vibrations in response to commands from the processor 60, and/or may include a speaker 66 capable of outputting tones or voice notifications generated by the processor 60. Notifications and information may include such things as notifying the user of a scheduled analyte measurement test, steps and procedures to be used to initiate an analyte measurement test, steps and procedures to be taken during the course of a test, errors that occurred during testing, test results such as the measurement results of the test, and the like.

One may use a visual display to provide such outputs, but this can be limiting, e.g., in that a display must be included in the device, the user must periodically consult the display by viewing it to check for notifications or information, etc. Moreover, particularly when the user is engaged in another activity, such as an exercise or work out program, it may be inconvenient or difficult to visually inspect the display. Accordingly, the output according to this aspect of the invention comprises an output that notifies the user or gets his or her attention in a manner other than, or in addition to, through a visual display. Preferred examples of such output mechanisms include audio notification, e.g., by broadcasting, one or more tones, a tune or jingle, a speaking voice, etc., and/or a vibratory or haptic notification.

As implemented in the illustrative preferred embodiment, device 10 comprises an audio output device 66, here comprising an amplifier and speaker for producing an audio tone, sequence of tones, a tune, a prerecorded speaking voice, etc. A vibratory or haptic device 68, for example, comprising an electric motor or haptic device, also is provided in body half 12a for providing a vibratory or pulse-based signal or notification to the user. Audio output device 66 and haptic device 68 are operatively coupled to and responsive to processor 60 via leads 70 and 72, respectively. They also are operatively coupled to power supply 40 via suitable leads (not shown).

Having now described the design and construction of wearable device 10, an example of a method of its operation will now be described. Prior to its use, information is pre-stored in the memory accessed by the processor 60, including a schedule for analyte testing.

Initially, the user wears the device in its normal configuration as a wearable, as shown in FIG. 2. At the time for a scheduled test, processor 60 causes audio device 66 and/or vibratory/haptic device 68 to activate, whereupon an audio signal (e.g., a tone, sequence of tones, a tune or jingle, a prerecorded voice, processor-generated voice, or the like), and/or a vibratory or haptic signal (in a form sufficient to alert the user) is issued by device 10 to the user.

Upon receiving this "Conduct Test Reminder" notification, the user moves breath collection tube 16 into position and places mouthpiece 18 into his or her mouth. The user then exhales into mouthpiece 18. The breath sample thus collected passes through mouthpiece 18, where any sediments, condensate droplets or other relatively large physical objects are filter out of the vapor stream. As the sample moves through the optional desiccant filter 30, moisture in the sample is removed to reduce its relative humidity. The breath sample then moves down tube 16 and into and through input conduit, and into main flow channel 46, where it contacts analyte sensor 50. Sensor 50 senses the chemical composition of the sample, including the target analyte, which in this illustrative example is acetone. The sample then continues to flow around sensor 50 and out exhaust port 48. As the sensor senses the breath sample, it outputs a signal to processor 60 representative of the measurement being taken. Processor 60 then processes this measurement signal to ascertain from the received measurement signal the presence and concentration of the target analyte. Processor 60 also performs a check for test validity, for example, as described in commonly-assigned U.S. patent application Ser. No. 14/807,828, entitled "Ketone Measurement System Capable Of Detecting And Notifying A User Of Proper Insertion Of Detachable Components," which is hereby incorporated by reference as if fully set forth herein.

In some embodiments, the wearable may discard an initial portion of the exhaled breath sample so that the measurements are based primarily on alveolar breath; for example, the processor 60 may activate a valve after the first two or three seconds of exhalation, causing the remaining portion of the breath sample to be routed to a breath collection/measurement chamber of the device.

The test results in this illustrative example are reported to the user in the following manner. Processor 60 causes audio device 66 to issue several audio tones to alert the user that the results available. Simultaneously, processor 60 causes vibratory or haptic device 68 to vibrate as a supplement to this notice, and to ensure the user's attention even if he or she is unable to hear the audio signal, e.g., in the event he or she is wearing headphones. After a short delay, e.g., perhaps of three to five seconds, processor 60, using audio device 66, causes a recorded or synthetic voice to announce the test results. After doing so, optionally, processor 60 may cause audio device 66 to announce supplemental information, e.g., parameters of the test, time of day, the date and time of the next scheduled test, and so on. Wearable 10 has been designed specifically to illustrate a simple or minimal and cost-effective version of devices according to this aspect of the invention. Processor 60 also stores the measurement result and related data.

As a modification, for example, one may add a display, e.g., such as a simple LED display, that can display the aforementioned test or measurement results and supplemental information, (e.g., those noted above, plus optionally graphical chart of results over time, error codes, etc.), as a supplement to the audio and/or vibratory notices.

Figure 7:
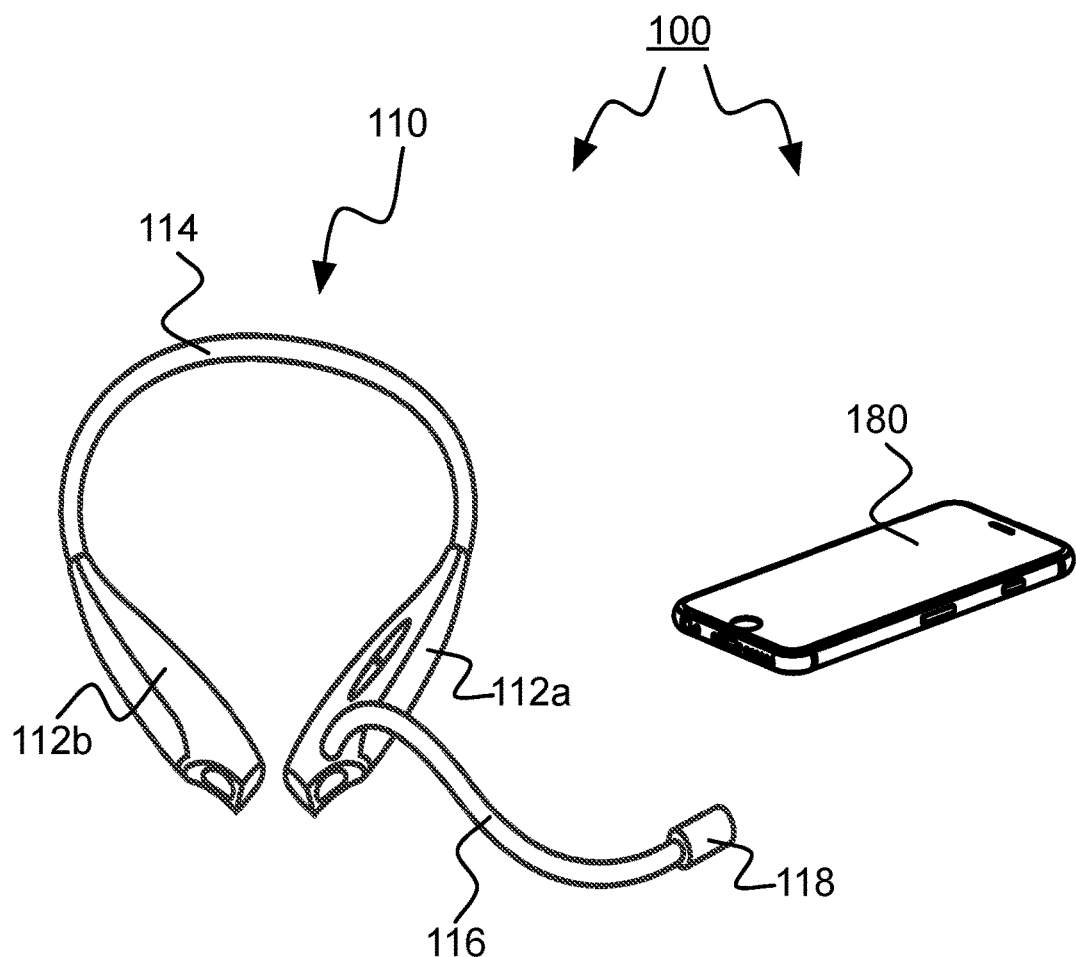
FIG. 7 shows a presently preferred system embodiment according to another aspect of the invention.

In accordance with another aspect of the invention, a presently preferred embodiment in the form of a system 100 will now be described. System 100, shown in pictorial view in FIG. 7, comprises a wearable 110 that in many respects is similar to or identical to wearable 10, and a command device 180 which, in this system embodiment, comprises a commercially-available smart phone. Previously-described wearable 10 is designed to be used and operated as a stand-alone device, separately or independently from other devices, although, as noted above, it could be modified to have an ability to communicate externally with other devices, such as with a smart phone, and to share functionality. In system 100, wearable 110 is designed to conduct the breath analysis testing, but many of the control and reporting functions are configured in the smart phone instead of the wearable itself. It should be noted that one may modify either of the designs described herein for wearable 10 and system 100 so that the various functionalities described herein are divided between the wearable and one or more external devices such as a smart phone.

Figure 8:
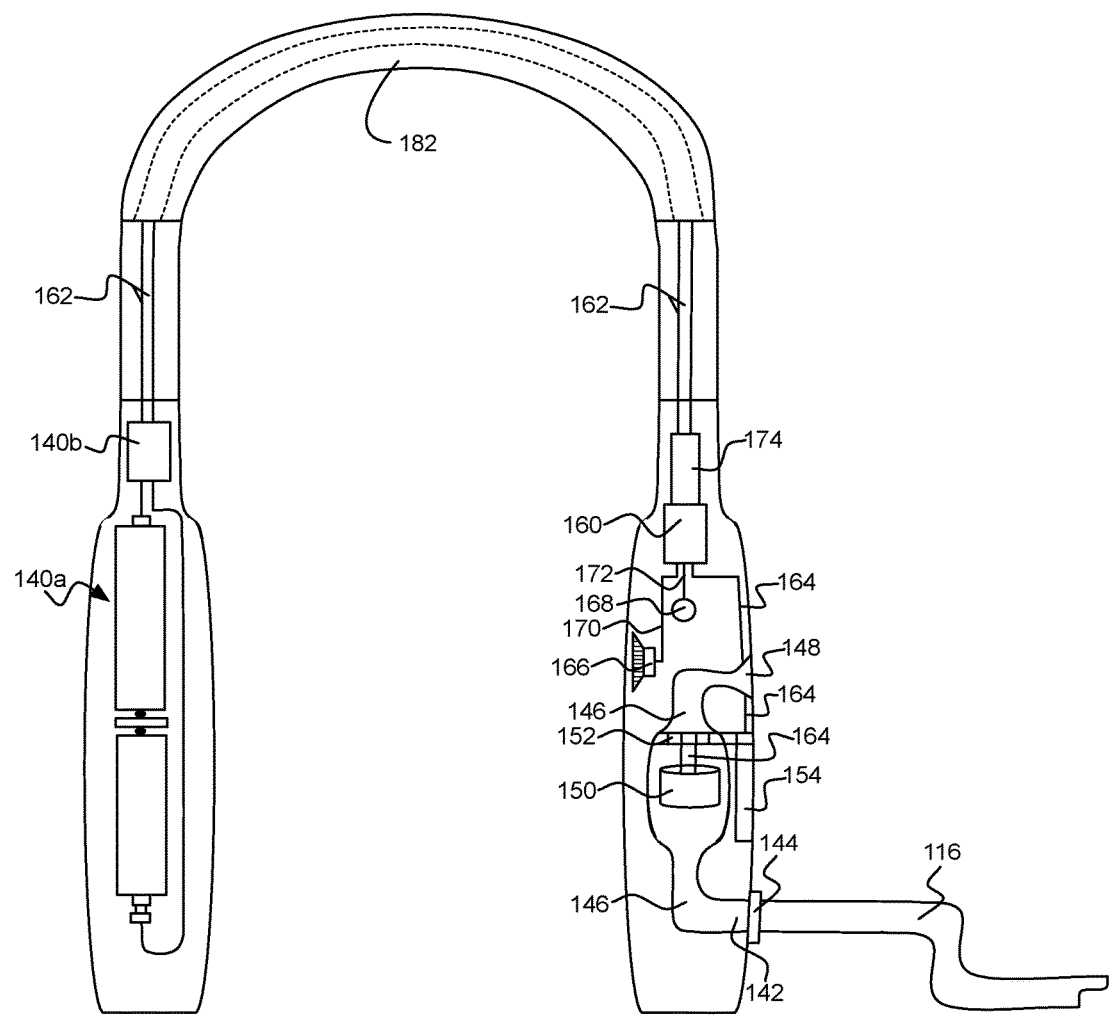
FIG. 8 shows a partial cutaway side view of the wearable of FIG. 7.

As noted herein above, wearable 110 is substantially similar to or the same as wearable 10. As shown in FIG. 8, it comprises a primary body half 112a, a secondary body half 112b, a connecting band 14, a breath collection tube 116 and a mouthpiece 118, all as described herein above with respect to wearable 10, as indicated by corresponding reference numerals and as shown in previous drawing figures. Wearable 110 also comprises an analyte sensor 150, a processor 160, audio output device 166 and a vibratory device 168, all as described herein above with respect to wearable 10.

Wearable 110 differs from wearable 10, however, in two significant respects. The first is that the functionality and associated programming and pre-storage of data in the memory accessed by the processor 160 is more limited than that of processor 60. The second is that wearable 110 comprises a wireless transceiver device 174 operatively coupled to processor 160, and to power supply 140 for power.

Command device 180 comprises a commercially-available smart phone, but also comprises a software application ("App") or other suitable software or programming to carry out the functionality as described herein. Prior analyte measurement results and data, test scheduling and so on are stored on command device 180. Command device 180 is programmed to monitor test schedule, issue commands to wearable 110 when a scheduled test is to be performed, receive test measurement results and related data, display the results and data, and store them. Processor 160, on the other hand, has more limited functionality that centers on performing the breath analyte testing and communicating with command device 180 to receive notifications and instructions and to transmit measurement results and possibly other data to command device 180. Preferably, and in this illustrative system 100 embodiment, wearable 110 retains the functionality and responsibility for providing audio and/or vibratory or haptic notifications as described herein above, in this instance, using audio device 166 and vibratory device 168. Optionally but preferably, command device 180 also may provide audio and vibratory notice as described herein as a supplement to those of wearable 110. Command device 180 also displays scheduling information, status of testing, test results, etc. on its built-in display, in addition to performing routine housekeeping and overhead functions (e.g., self-test, reliability checks, etc.) for both the wearable and itself as it relates to the system app for this system. The wearable may double as a Bluetooth headset, in which case the Command device (via its App) generates voice-over notifications that are output via the wearable while the volume of any music or call is temporarily lowered.

To illustrate the functionality of system 100, the following illustrative operation of it will now be presented. At command device 180, the pre-stored test schedule for the user is monitored and, when the schedule date and time of a test arrives, command device 180 provides notification to the user to conduct an analyte measurement test. This notification is provided on the display of the command device 180, and via its transmission link with wearable 110, also at wearable 110. The notification provided by wearable 110 comprises audio and/or vibratory notifications as described herein above with respect to wearable 10. It also may comprise displaying the notice on the display of wearable 110 if one is provided.

Upon this notification, the user initiates an analyte measurement test. Optionally, one or more audio commands or instructions may be provided to the user to walk him or her through the testing steps and procedures. These commands and instructions may be pre-stored at wearable 110, e.g., in processor 160, or at command device 160 and presented to the use by device 160, or some combination of these.

At the wearable 110, it receives the Start Test command or instruction, indicates a Ready notification to the user via an audio (tone, etc.) and/or vibratory or haptic notification (pulse, etc.). Upon this notification, the user performs the analyte measurement test by exhaling into the tube 116, as generally described herein above.

Instead of a pre-stored time schedule, the command device 180 may prompt the user to perform a test based on other factors such as the magnitude of prior measurements, the time since the prior measurement was performed, the user's heart rate, information from a medical device (such as an insulin pump or continuous glucose monitor), the user's location, or the user's diet journal. Examples of how to time a test, or reasons to increase or decrease the frequency of a test are described elsewhere, such as U.S. Provisional Pat. Appl. Nos. 62/338,312 entitled "Ketone Measurement System For Monitoring Medical Condition", 62/408,208 entitled "Artificial Intelligence Based Health Coaching Based On Ketone Levels Of Participants", and U.S. Pat. No. 9,486,169, entitled "Ketone Measurement System And Related Method With Accuracy And Reporting Enhancement Features" and U.S. Pat. No. 9,341,632, entitled "Ketone Measurement System Capable Of Detecting Correlations Between Measurements And User Behaviors", all of which are hereby incorporated by reference as if fully set forth herein.

The breath analysis device of wearable 110, which comprises analyte sensor 150, performs breath analysis and provides the measurement signal to microprocessor 160. Microprocessor 160 performs necessary processing on the measurement signal as described herein above and then, via transceiver device 174, transmits the measurement signal to command device 180. Command device 180, under control of the app, records the measurement result and (optionally) associated data, such as test date and time, displays the result on its display, and causes an audio and/or vibratory notification to be provided at the command device, the wearable, and preferably both, that the measurement results are available and are being displayed. The command device 180 may also wirelessly transmit the results to the wearable 110 as an audio (voice) message that is played by the wearable.

Referring to FIG. 8, the flexible member 182 may be or comprise a material that is elastic and can be "bent" to conform to the shape of an article of clothing or a part of the body. As shown in FIG. 8, the flexible member may not fully clasp the wearable to itself. In contrast with this, referring to FIG. 9, the flexible member 200 allows the wearable to fully clasp around itself, here the wrist.

Figure 9:
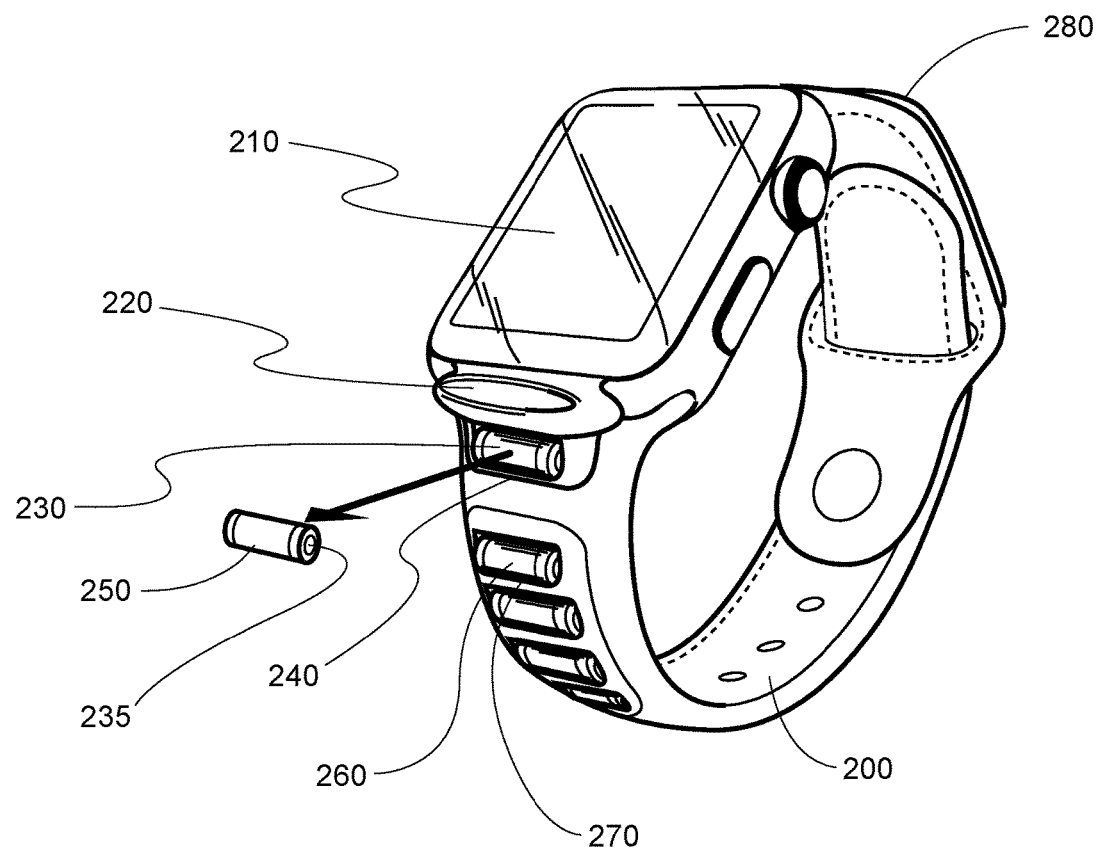
FIG. 9 shows an embodiment of a wearable that may be worn around the wrist.

Further describing FIG. 9, the wearable is a watch that comprises a breath analysis measurement system. The watch may, for example, include functionality typically included in smart watches, such as the ability to communicate wirelessly with a smartphone and to execute mobile applications that interact with the smartphone. One such mobile application may include functionality for tracking, tagging and reporting measurements, and for generating various types of reminders, as described, for example, in U.S. Pat. No. 9,351,684, entitled "Ketone Measurement System With User Interface For Efficient Categorization Of Measurements", the disclosure of which is hereby incorporated by reference as if fully set forth herein. This mobile application may also include diet tracking functionality. In this embodiment of FIG. 9, the strap 200 is modified to include at least one chemical sensor 230 and a breath sample collection device 220. (As shown in the figure, the breath sample collection device may be as simple as a mouthpiece, but this is not intended to be limiting.) It further comprises a display 210 that is used to communicate the timing or result of the measurement to the user. The display is optional, as the user could be prompted through a substitute component such as a haptic sensor worn around the wrist. The display may also be used to provide measurement reminders, to display measurement histories, to enable users to tag measurements, and to implement other mobile application functionality of the type described in the '684 patent referenced above.

The chemical sensor may be a multi-use sensor, such as a semiconductor sensor or a nanoparticle sensor. The term "multi-use sensor" includes sensors that do not consume chemical reagents, at least in a way that requires that they be eternally replenished with each test. As such, if an enzyme or aptamer can be regenerated, it would fall within the scope of a multi-use sensor. Alternatively, the chemical sensor may require that chemical reagents be replenished with each test, such as in the case of a colorimetric reactant that utilizes a developer solution.

Alternatively, the chemical sensor may be or comprise a capture sensor, which binds or adsorbs the analyte to the sensor. In such a configuration, the sensor stores the analyte and it is analyzed subsequently, such as with a separate reader device. Breath analysis devices that use a capture device and a reader device are described elsewhere, e.g., U.S. Provisional Pat. Appl. No. 62/396,240, entitled "Breath Analysis System With Rapid, Disposable Cartridge", which is hereby incorporated by reference as if fully set forth herein. The capture sensor may store the analyte from one measurement or a plurality of measurements (spaced over time). A plurality of measurements would be useful to report an aggregate production amount or production rate to the user.

The chemical sensor may be or comprise a single-use chemical sensor. In such a configuration, the single-use chemical sensor is not suitable for a repeat measurement or repeat capture.

For embodiments that utilize a capture sensor or a single-use chemical sensor, the wearable may include receptables (240, 270, and so on) for a plurality of cartridges. Such a wearable may be used in conjunction with a plurality of sensors 230 and 260 (and so on). If sensor 230 is removed (e.g., to position 250), it is no longer in the receptable 240.

In the embodiment of FIG. 9, each cartridge may be a one-time-use analyte sensor that is used to analyze a single breath sample, in which case the cartridge may contain an interactant material that interacts with one or more ketones in the breath sample. Each such cartridge may be analyzed by the wearable device itself to produce a measurement, or may be analyzed subsequently using a separate reader device as described above. The user in this embodiment is responsible for placing an unused cartridge into the "active" receptacle position, which places the cartridge in fluid communication with the breath input port and thus allows the cartridge to receive a breath sample as the user blows into the wearable device. In some implementations the wearable device may be capable of reading a unique ID of each cartridge and associating that ID with a time/date of the measurement.

Embodiments that utilize a multi-use sensor, such as a nanoparticle or semiconductor sensor, may utilize a plurality of receptacles (240, 270, and so on). In this configuration, each sensor may measure a different analyte or be used to represent a different category of measurements (a child's readings, or post-exercise readings).

The wearable may comprise a storage location 280 for sensors that are either ready for analysis or extra sensors.

One skilled in the art would appreciate that the different types of sensors and timing sequence described with regards to FIG. 9 may apply to FIG. 8 as well.

It will be appreciated that the invention is not limited to the specific embodiments and method implementations described herein. Variations and other embodiments and methods may be made within the scope of the invention.

The various features described in connection with the headset type embodiments of FIGS. 1-8 can be incorporated into the watch embodiments described in connection with FIG. 9, and vice versa. For example, the haptic features of the headset embodiments may be incorporated into the watch embodiments, and the removable cartridge and cartridge storage features of the watch embodiment of FIG. 9 may be included in the headset embodiments. More generally, each embodiment described herein can be modified to include one or more features of other disclosed embodiments. All resulting combinations of features are contemplated and form part of this disclosure.

The various functionality of the wearable devices described herein may be controlled by program code executed by a processor of the wearable device. The program code may be stored in a non-volatile memory (one type of non-transitory storage medium) of the wearable device.

What is claimed is:

1. A wearable breath analysis device, comprising:
 a housing that comprises a breath input port and a flexible watch band that is configured to bend to conform to a wrist of a user, wherein the watch band comprises a plurality of receptacles configured to hold a plurality of breath analysis cartridges, wherein the housing additionally includes an active receptacle into which a single breath analysis cartridge of the plurality of breath analysis cartridges can be inserted to place the breath analysis cartridge in fluid communication with the breath input port, such that an analyte in a breath sample exhaled into the breath input port is captured in the single breath analysis cartridge;
 a notification device operatively configured to provide at least one of a haptic notification or an auditory notification to the user; and
 a processor that is configured to control the notification device to provide at least one type of notification to the user.

2. The wearable breath analysis device of claim 1, wherein the watch band additionally includes a cartridge storage container capable of holding a plurality of used breath analysis cartridges.

3. The wearable breath analysis device of claim 1, in combination with a reader device that is separate from the wearable breath analysis device, the reader device configured to analyze used breath analysis cartridges to generate corresponding analyte measurements.

4. The wearable breath analysis device of claim 1, wherein the processor executes an application that provides interactive functionality for the user, via a watch display, to at least view, track, and tag ketone measurements.

5. The wearable breath analysis device of claim 1, wherein the processor is configured to use the notification device to provide measurement reminders to the user according to a schedule.

6. The wearable breath analysis device of claim 1, further comprising the plurality of breath analysis cartridges, wherein each breath analysis cartridge is a single-use cartridge containing an interactant material that interacts with an analyte in the breath sample.

7. The wearable breath analysis device of claim 6, wherein each breath analysis cartridge comprises a solid state sensor.

8. The wearable breath analysis device of claim 1, further comprising a wireless transceiver, wherein the processor is programmed to communicate via the wireless transceiver with a command device.

9. The wearable breath analysis device of claim 8, wherein the processor is configured to report breath analysis measurements to the command device.

10. The wearable breath analysis device of claim 1, wherein the notification device is capable of providing both haptic notifications and auditory notifications.

11. The wearable breath analysis device of claim 1, wherein the breath input port comprises a mouthpiece.

* * * * *